US007513909B2

(12) United States Patent
Lane et al.

(10) Patent No.: US 7,513,909 B2
(45) Date of Patent: Apr. 7, 2009

(54) TWO-PIECE PROSTHETIC VALVES WITH SNAP-IN CONNECTION AND METHODS FOR USE

(75) Inventors: Ernest Lane, Huntington Beach, CA (US); Shouyan Lee, Rancho Santa Margarita, CA (US); Charles Huang, Villa Park, CA (US)

(73) Assignee: Arbor Surgical Technologies, Inc., Irvine, CA (US)

( * ) Notice: Subject to any disclaimer, the term of this patent is extended or adjusted under 35 U.S.C. 154(b) by 198 days.

(21) Appl. No.: 11/279,246

(22) Filed: Apr. 10, 2006

(65) Prior Publication Data

US 2006/0235508 A1    Oct. 19, 2006

Related U.S. Application Data

(60) Provisional application No. 60/669,704, filed on Apr. 8, 2005.

(51) Int. Cl.
A61F 2/24 (2006.01)
(52) U.S. Cl. ....................................................... 623/2.4
(58) Field of Classification Search .................. 623/2.4, 623/2.38, 2.1
See application file for complete search history.

(56) References Cited

U.S. PATENT DOCUMENTS

| 3,371,352 A | 3/1968 | Siposs |
| 3,464,065 A | 9/1969 | Cromie |
| 3,571,815 A | 3/1971 | Somyk |
| 3,574,865 A | 4/1971 | Hamaker |
| 3,686,740 A | 8/1972 | Shiley |
| 3,744,060 A | 7/1973 | Bellhouse |
| 3,800,403 A | 4/1974 | Anderson |
| 3,839,741 A | 10/1974 | Haller |
| 3,996,623 A | 12/1976 | Kaster |
| 3,997,923 A | 12/1976 | Possis |

(Continued)

FOREIGN PATENT DOCUMENTS

DE        19532973 C1    11/1996

(Continued)

OTHER PUBLICATIONS

Mohammed Abdoolcarim, Thomas Guillaume, Emily Ma; ME294: Replaceable Heart Valve Project, Dec. 12, 2002.

*Primary Examiner*—Bruce E Snow
(74) *Attorney, Agent, or Firm*—William A. English; Vista IP Law Group LLP

(57) ABSTRACT

A prosthetic heart valve assembly includes a gasket member and a valve member including a plurality of fasteners and a plurality of engagement members corresponding to the fasteners. The fasteners and/or engagement members may be configured to guide the engagement members into engagement with the fasteners. For example, the fasteners may include U-shaped spring-biased clips, e.g., attached to a core or other portion of a sewing cuff of the gasket member, and the engagement members may include latches or barbed protrusions that engage one or more holes in the fasteners. During use, the gasket member is introduced into a tissue annulus, and secured to the annulus, e.g., using a plurality of clips directed through the sewing cuff. The valve member is then introduced into the annulus and the engagement members are snapped or otherwise guided into engagement with the fasteners to secure the valve member relative to the gasket member.

24 Claims, 13 Drawing Sheets

U.S. PATENT DOCUMENTS

| | | |
|---|---|---|
| 4,035,849 A | 7/1977 | Angell |
| 4,245,358 A | 1/1981 | Moasser |
| 4,259,753 A | 4/1981 | Liotta |
| 4,451,936 A | 6/1984 | Carpentier |
| 4,485,816 A | 12/1984 | Krumme |
| 4,535,483 A | 8/1985 | Klawitter |
| 4,548,202 A | 10/1985 | Duncan |
| 4,680,031 A | 7/1987 | Alonso |
| 4,692,164 A | 9/1987 | Dzemeshkievich |
| 4,705,516 A | 11/1987 | Barone |
| 4,725,274 A | 2/1988 | Lane |
| 4,790,843 A | 12/1988 | Carpentier |
| 4,851,000 A | 7/1989 | Gupta |
| 4,892,541 A | 1/1990 | Alonso |
| 4,994,077 A | 2/1991 | Dobben |
| 5,032,128 A | 7/1991 | Alonso |
| 5,037,434 A | 8/1991 | Lane |
| 5,071,431 A | 12/1991 | Sauter |
| 5,147,391 A | 9/1992 | Lane |
| 5,178,633 A | 1/1993 | Peters |
| 5,192,303 A | 3/1993 | Gatturna |
| 5,370,685 A | 12/1994 | Stevens |
| 5,469,868 A | 11/1995 | Reger |
| 5,549,665 A | 8/1996 | Vesely |
| 5,573,543 A | 11/1996 | Akopov |
| 5,607,470 A | 3/1997 | Milo |
| 5,669,917 A | 9/1997 | Sauer |
| 5,716,370 A | 2/1998 | Williamson |
| 5,720,755 A | 2/1998 | Dakov |
| 5,725,554 A | 3/1998 | Simon |
| 5,776,188 A | 7/1998 | Shepherd |
| 5,860,992 A | 1/1999 | Daniel |
| 5,891,160 A | 4/1999 | Williamson |
| 5,935,163 A | 8/1999 | Gabbay |
| 5,976,183 A | 11/1999 | Ritz |
| 5,984,959 A | 11/1999 | Robertson |
| 6,042,607 A | 3/2000 | Williamson |
| 6,045,576 A | 4/2000 | Starr |
| 6,059,827 A | 5/2000 | Fenton |
| 6,066,160 A | 5/2000 | Colvin |
| 6,096,074 A | 8/2000 | Pedros |
| 6,106,550 A | 8/2000 | Magovern |
| 6,126,007 A | 10/2000 | Kari |
| 6,143,025 A | 11/2000 | Stobie |
| 6,162,233 A | 12/2000 | Williamson |
| 6,176,877 B1 | 1/2001 | Buchanan |
| 6,197,054 B1 | 3/2001 | Hamblin, Jr. |
| 6,200,306 B1 | 3/2001 | Klostermeyer |
| 6,203,553 B1 | 3/2001 | Robertson |
| 6,217,611 B1 | 4/2001 | Klostermeyer |
| 6,241,765 B1 | 6/2001 | Griffin |
| 6,254,636 B1 | 7/2001 | Peredo |
| 6,287,339 B1 | 9/2001 | Vazquez |
| 6,309,417 B1 | 10/2001 | Spence |
| 6,319,281 B1 | 11/2001 | Patel |
| 6,358,556 B1 | 3/2002 | Ding |
| 6,371,983 B1 | 4/2002 | Lane |
| 6,391,053 B1 | 5/2002 | Brendzel |
| 6,402,780 B2 | 6/2002 | Williamson |
| 6,409,759 B1 | 6/2002 | Peredo |
| 6,425,916 B1 | 7/2002 | Garrison |
| 6,447,524 B1 | 9/2002 | Knodel |
| 6,454,799 B1 | 9/2002 | Schreck |
| 6,461,382 B1 | 10/2002 | Cao |
| 6,468,305 B1 | 10/2002 | Otte |
| 6,709,457 B1 | 3/2004 | Otte |
| 6,716,244 B2 | 4/2004 | Klaco |
| 6,776,785 B1 | 8/2004 | Yencho |
| 6,790,229 B1 | 9/2004 | Berreklouw |
| 6,893,459 B1 | 5/2005 | Macoviak |
| 6,939,365 B1 | 9/2005 | Fogarty |
| 7,083,648 B2 | 8/2006 | Yu |
| 7,172,625 B2 | 2/2007 | Shu |
| 7,175,659 B2 | 2/2007 | Hill |
| 7,201,771 B2 | 4/2007 | Lane |
| 2002/0055774 A1 | 5/2002 | Liddicoat |
| 2002/0123802 A1 | 9/2002 | Snyders |
| 2002/0128684 A1 | 9/2002 | Foerster |
| 2002/0183834 A1 | 12/2002 | Klaco |
| 2003/0023302 A1 | 1/2003 | Moe |
| 2003/0045902 A1 | 3/2003 | Weadeock |
| 2003/0109922 A1 | 6/2003 | Peterson |
| 2004/0015232 A1 | 1/2004 | Shu |
| 2004/0030381 A1 | 2/2004 | Shu |
| 2004/0044406 A1 | 3/2004 | Woolfson |
| 2004/0122514 A1 | 6/2004 | Fogarty |
| 2004/0122516 A1 | 6/2004 | Fogarty |
| 2004/0176839 A1 | 9/2004 | Huynh |
| 2004/0210305 A1 | 10/2004 | Shu |
| 2004/0225356 A1 | 11/2004 | Frater |
| 2005/0043760 A1 | 2/2005 | Fogarty |
| 2005/0080454 A1 | 4/2005 | Drews |
| 2005/0137686 A1 | 6/2005 | Salahieh |
| 2005/0137691 A1 | 6/2005 | Salahieh |
| 2005/0137695 A1 | 6/2005 | Salahieh |
| 2005/0137696 A1 | 6/2005 | Salahieh |
| 2005/0159811 A1 | 7/2005 | Lane |
| 2005/0165479 A1 | 7/2005 | Lane |
| 2005/0240263 A1 | 10/2005 | Fogarty |
| 2006/0095125 A1* | 5/2006 | Chinn et al. ................. 623/2.4 |
| 2006/0122634 A1 | 6/2006 | Ino |
| 2006/0154230 A1 | 7/2006 | Cunanan |
| 2006/0195184 A1 | 8/2006 | Lane |
| 2006/0195185 A1 | 8/2006 | Lane |
| 2006/0195186 A1 | 8/2006 | Drews |
| 2006/0276888 A1 | 12/2006 | Lee |

FOREIGN PATENT DOCUMENTS

| | | |
|---|---|---|
| EP | 1088529 | 4/2001 |
| WO | 9915112 A1 | 4/1999 |
| WO | 0044311 A2 | 8/2000 |
| WO | 0056250 A1 | 9/2000 |
| WO | 0059382 A1 | 10/2000 |
| WO | 0064380 A1 | 11/2000 |
| WO | 0110310 A1 | 2/2001 |
| WO | 0110312 A1 | 2/2001 |
| WO | 0158363 A1 | 8/2001 |
| WO | 0182840 A | 11/2001 |
| WO | 0187190 A2 | 11/2001 |
| WO | 2004006810 A | 1/2004 |
| WO | 2005039452 | 5/2005 |

* cited by examiner

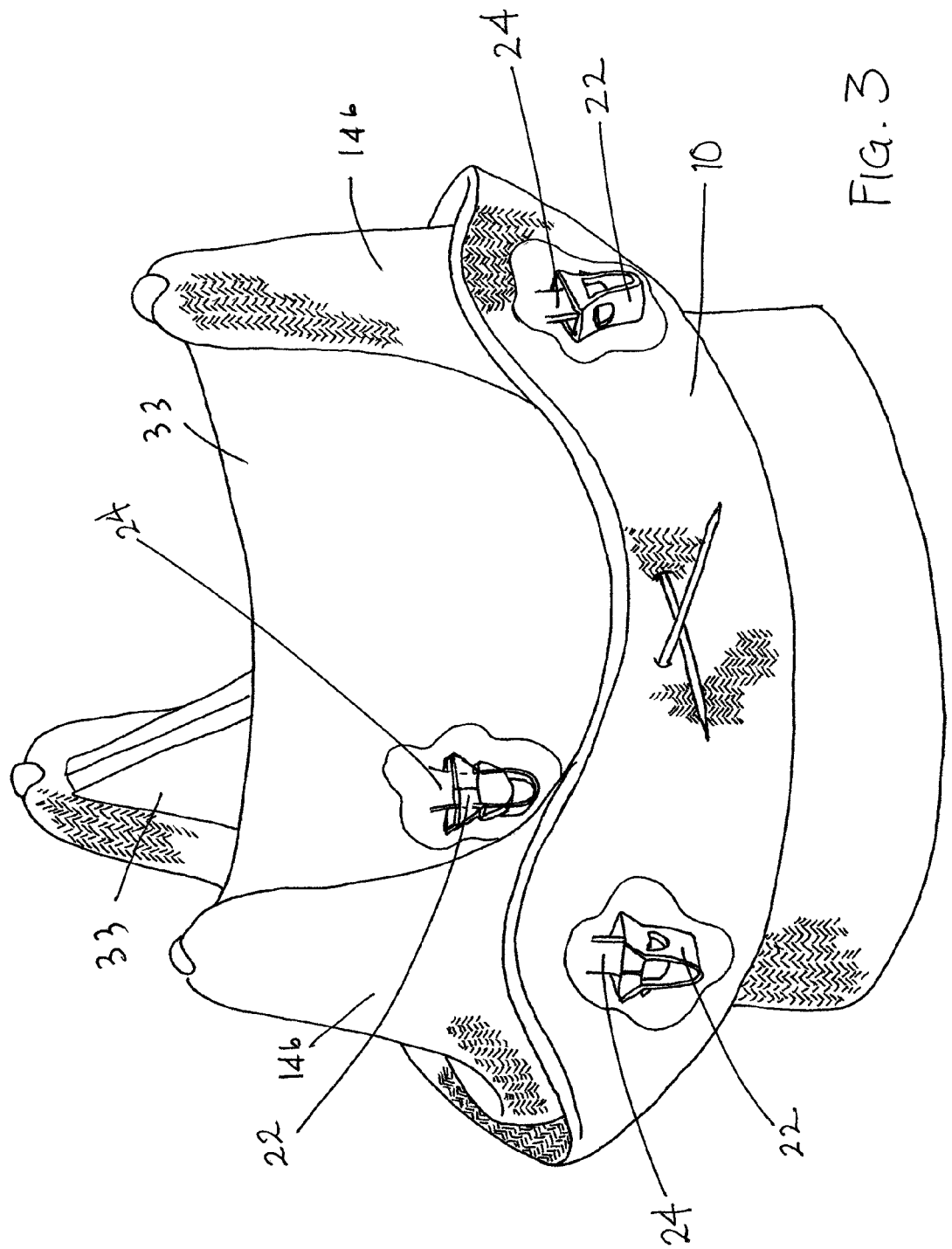

TWO-PIECE PROSTHETIC VALVES WITH SNAP-IN CONNECTION AND METHODS FOR USE

The present application claims benefit of provisional application Ser. No. 60/669,704, filed Apr. 8, 2005, the entire disclosure of which is expressly incorporated by reference herein.

FIELD OF THE INVENTION

The present invention generally relates to prosthetic valves, and, more particularly, relates to two-piece prosthetic valves, and to methods for making and using them.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and eventual calcification of the valve structure.

To address this concern, flexible sewing rings have been suggested for use with multiple component valves. The sewing ring may be implanted within the annulus, e.g., using the procedure described above, i.e., parachuting the sewing ring down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

SUMMARY

The present invention is directed generally to prosthetic valves, and, more particularly, to two-piece prosthetic valves, and to methods for making and using them.

In accordance with one embodiment, a prosthetic heart valve assembly is provided that includes a gasket member and a valve member including a plurality of fasteners and a plurality of engagement members corresponding to the fasteners. The fasteners and/or engagement members may be configured to guide the engagement members into engagement with the fasteners. For example, the engagement members may include ramped first edges and blunt second edges and the fasteners may define pockets for receiving the engagement members, the ramped edges guiding the engagement members into the pockets and the blunt edges preventing subsequent removal of the engagement members from the fasteners.

In an exemplary embodiment, the fasteners may include U-shaped spring-biased clips, and the engagement members may include latches or barbed protrusions that engage one or more holes or in the clips. For example, the fasteners may be attached to a core or other portion of a sewing cuff of the gasket member, and the engagement members may be integrally formed as part of a frame of the valve member.

In accordance with another embodiment, a method is provided for implanting a prosthetic valve assembly within a tissue annulus, e.g., adjacent or within a site of a native valve, such as a aortic valve annulus. A gasket member may be introduced into the annulus and secured to tissue surrounding the annulus, e.g., using a plurality of clips or other fasteners. A valve member may then be introduced into the annulus and directed towards the gasket member. The gasket member and valve member may include corresponding engagement members and fasteners for securing the valve member relative to the gasket member.

In an exemplary embodiment, the fasteners on one of the gasket member and the valve member may be configured for guiding the fasteners on the other of the gasket member and the valve member as valve member is directed towards the gasket member. For example, the fasteners may include clips or other receptacles and the engagement members may include ramped and blunt edges. As the valve member is directed towards the gasket member, the ramped edges may slidable along the fasteners until the engagement members are engaged with the fasteners. The blunt edges may prevent subsequent removal of the engagement members from the fasteners, thereby securing the valve member relative to the gasket member.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 3 is a perspective view of the valve member of FIG. 2 secured to the gasket member of FIG. 1, to provide an assembled heart valve assembly.

DETAILED DESCRIPTION

Figure 1:
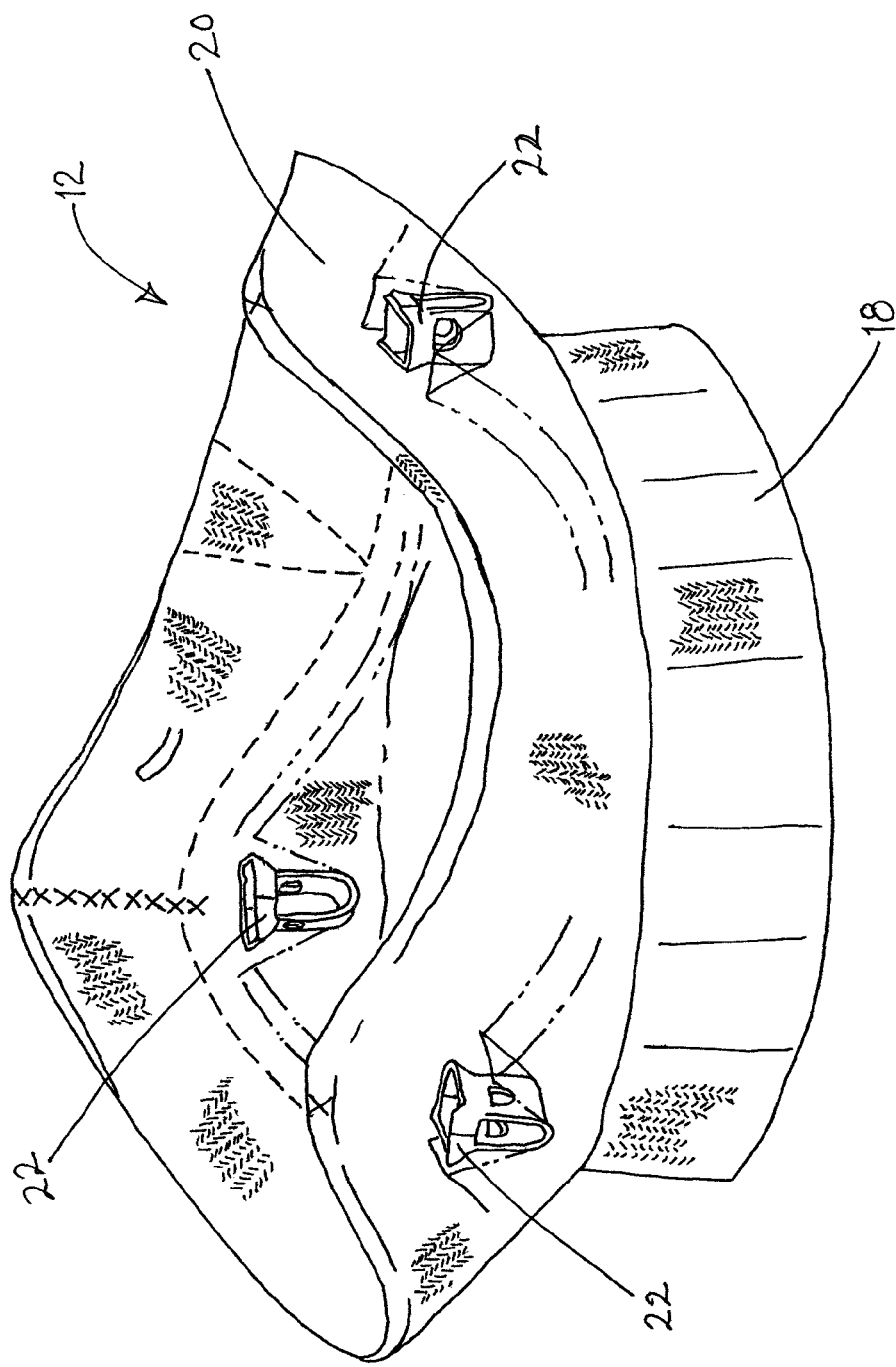
FIG. 1 is a perspective view of a gasket member including three fasteners.
Figure 2:
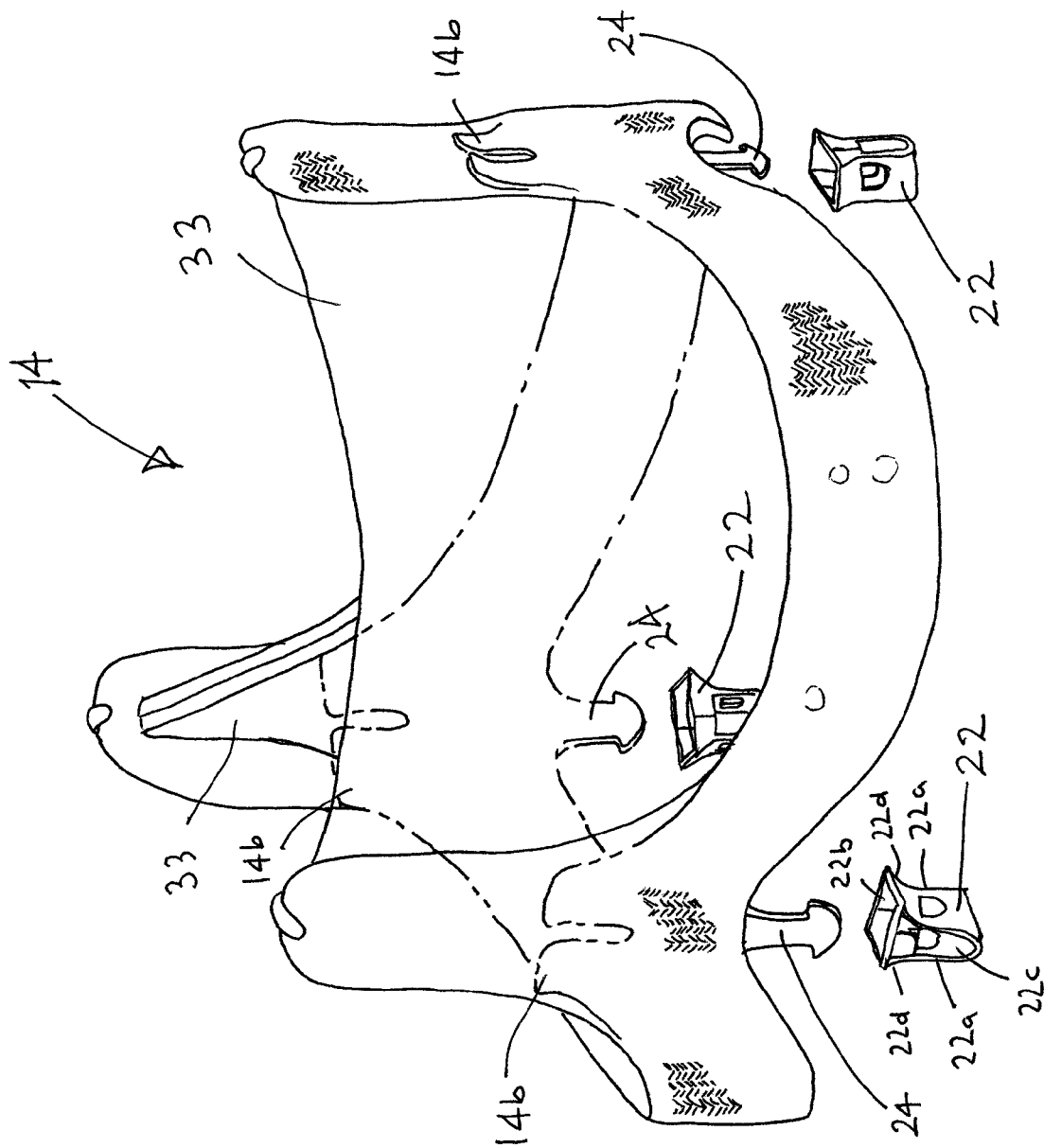
FIG. 2 is a perspective view of a crown or valve member including fasteners for engaging with the fasteners in the gasket member of FIG. 1.

Turning to the drawings, FIGS. 1-3 show an exemplary embodiment of a heart valve assembly 10 that generally includes a base or gasket member 12 (best seen in FIG. 1) and a crown or valve member or 14 (best seen in FIG. 2). The gasket member 12 is generally an annular shaped body, which may have a substantially circular or noncircular shape, such as a multiple lobular shape. The gasket member 12 and valve member 14 include a plurality of fasteners 22 and engagement members 24, e.g., in corresponding sets, as explained further below.

In one embodiment, as shown in FIG. 1, the gasket member 12 may have a lower portion having a substantially circular shape, and an upper or outer portion having a multiple lobular shape, e.g., a tri-lobular shape (i.e., including three lobes separated by cusps or scallops). The shape may correspond generally to a cross-section of a biological annulus within which the gasket member 12 may be implanted. It will be appreciated that the gasket member 12 may define other noncircular shapes that may correspond to the anatomy of a patient within which the heart valve assembly 10 is to be implanted.

The gasket member 12 may include an annular ring or frame 18 and a flexible cuff or sewing ring 20 that may extend radially outwardly around a periphery of the annular ring 18. Optionally, the gasket member 12 may include other components, e.g., a stand-off or collar (not shown), such as those disclosed in applications Ser. Nos. 60/685,265, filed May 27, 2005, and 60/743,185, filed Jan. 27, 2006, the entire disclosures of which are expressly incorporated by reference herein.

The annular ring 18 may be substantially rigid, e.g., retaining its shape, or semi-rigid, e.g., such that the annular ring 18 may be resiliently deformed, e.g., to conform at least partially to the anatomy within which the gasket member 12 is implanted. In addition or alternatively, the annular ring 18 may be elastically or super-elastically deformable, e.g., compressible from its relaxed, expanded configuration into a lower profile configuration, yet resiliently biased to return to the expanded configuration shown when released.

In another alternative, the annular ring 18 may be formed from a shape memory material, e.g., Nitinol, having the expanded configuration heat treated or otherwise programmed into the material. For example, the material of the annular ring 18 may undergo substantial martensitic transformation, e.g., when cooled to a temperature approaching zero degrees Celsius (0° C.), wherein the gasket member 12 may be substantially soft and plastically deformable. When warmed, the material may complete austenitic transformation, e.g., at a temperature below 98° C., such that the gasket member 12 "remembers" its original expanded configuration, and becomes resiliently biased towards the expanded configuration expand from the lower profile configuration. Thus, the gasket member 12 may be cooled to transform the annular ring 18 to a substantially martensitic state to facilitate radial compression of the gasket member 12 for delivery, and warmed, e.g., when exposed to body temperature of a patient, to a substantially austenitic state whereupon the gasket member 12 may become biased to resiliently return towards its original expanded condition upon being released at an implantation site.

Figure 7:
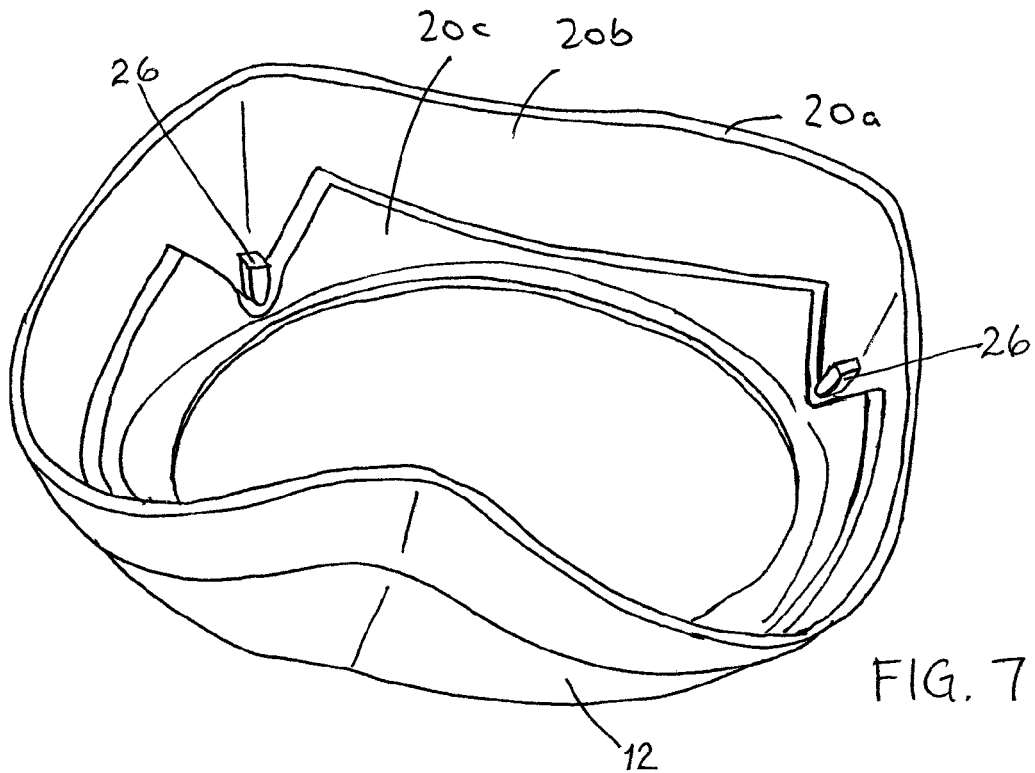
FIGS. 7 and 8 are perspective views of a flexible core for a sewing cuff that may be included in the gasket member of FIG. 4, shown before and after attaching fasteners to the core.
Figure 8:
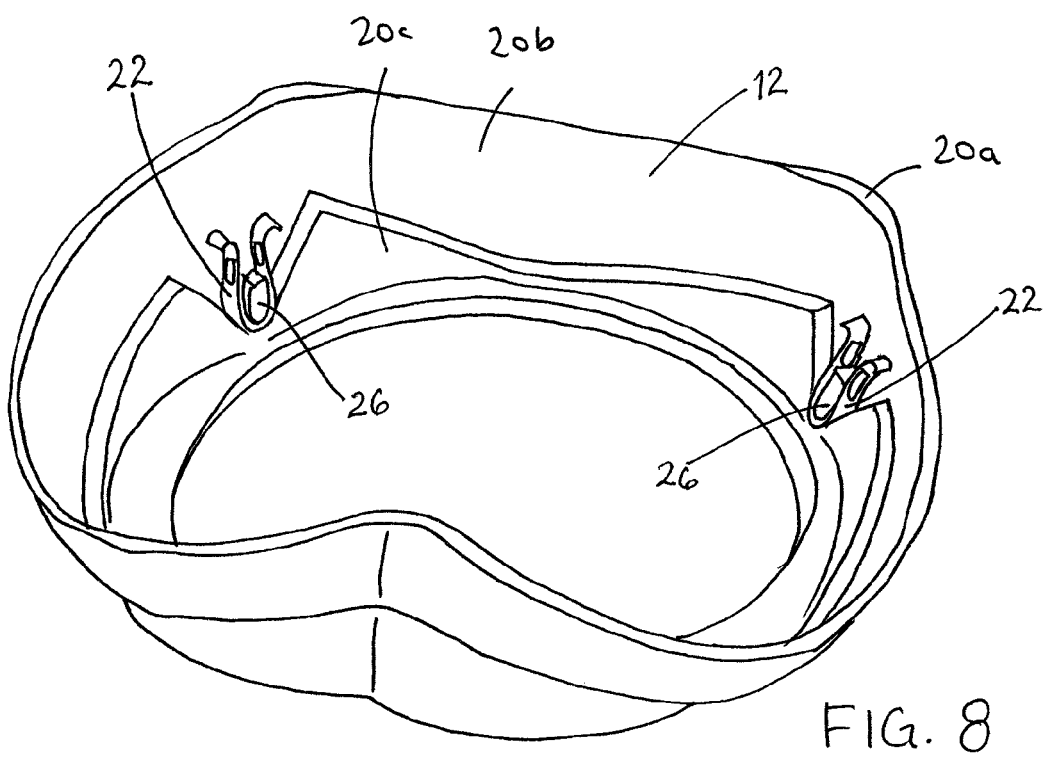

Turning to FIGS. 7 and 8, the cuff 20 generally includes a flexible core 20a, which may be at least partially covered by fabric (not shown, see, e.g., FIG. 1). In exemplary embodiments, the core 20a may be formed from resiliently flexible material, such as silicone or other elastomeric materials. The core 20a may be solid or may include a lattice. Alternatively, the cuff 20 may simply be one or more layers of fabric or other material extending from and/or covering at least a portion of the annular ring 18.

Figure 4:
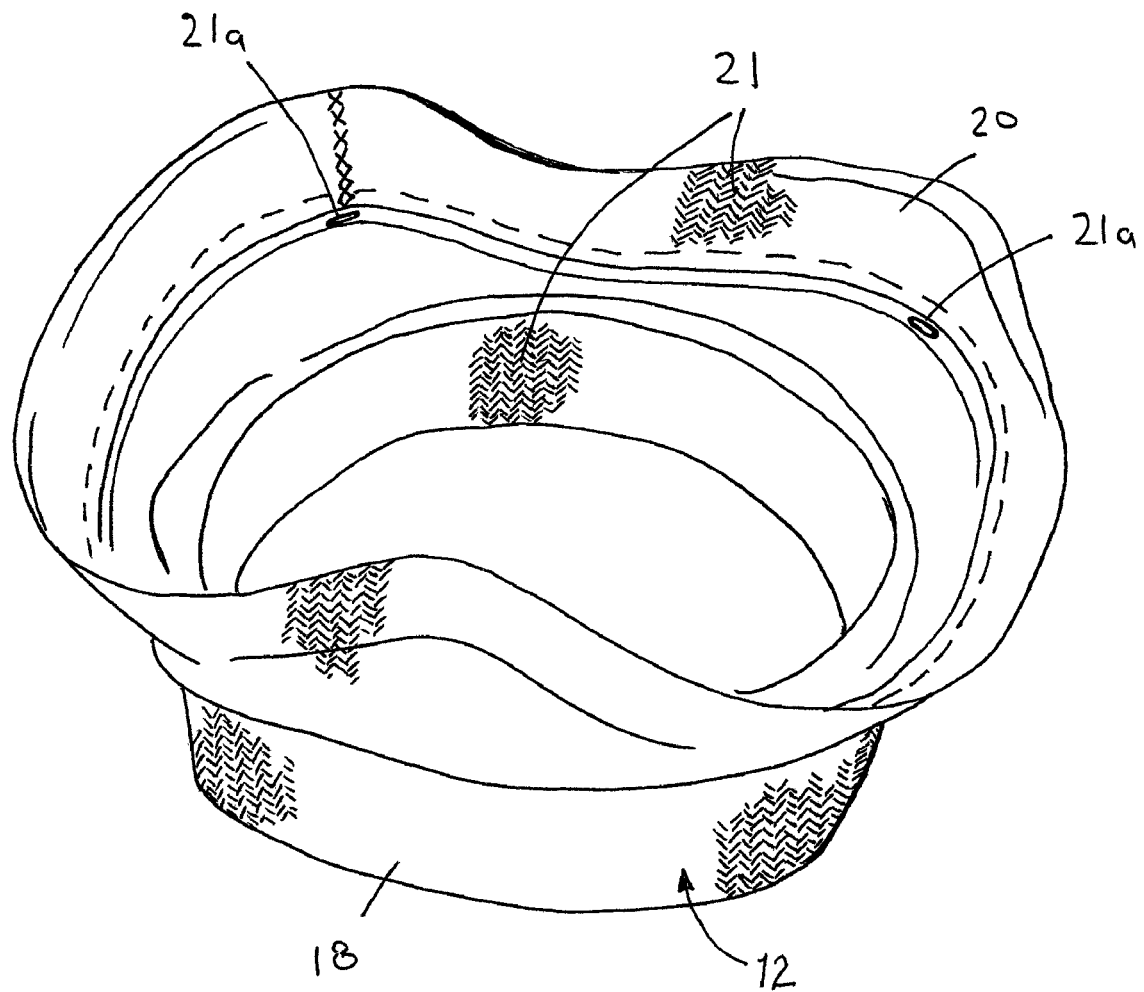
FIG. 4 is a perspective view of a gasket member including a cloth covering overlying a flexible core and annular ring.

In addition, a layer of fabric (not shown) may cover all or a portion of core 20a and/or the annular ring 18, e.g., other than any connectors and/or bearing surfaces, e.g., for securing the valve member 14 to the gasket member 12, as described further elsewhere herein. For example, FIG. 4 shows a layer of fabric 21 substantially covering the components of the gasket member 12. As shown, the fabric covering 21 includes a plurality of holes 21a (e.g., button holes), which may be disposed above or otherwise adjacent the fasteners 22 (not shown in FIG. 4; see, e.g., FIG. 1).

The annular ring 18 and cuff 20 may be integrally formed as a single component or may be separate components attached to one another. In addition, the cuff 20 may be slidably or fixedly attached to the annular ring 18. Additional information on exemplary gasket members and methods for making and using them are disclosed in co-pending application Ser. No. 11/069,081, filed Feb. 28, 2005, the entire disclosure of which is expressly incorporation by reference herein.

Figure 2A:
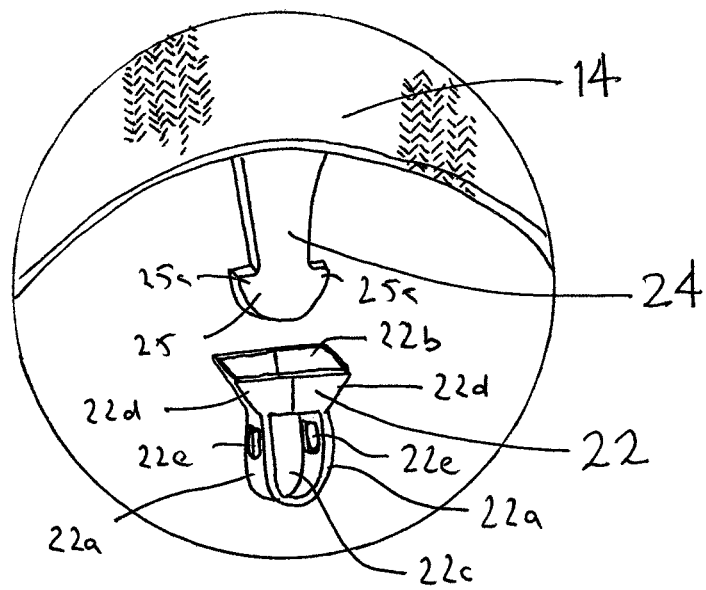
FIGS. 2A-2C are details showing the engagement of one set of the fasteners shown in FIGS. 1 and 2.
Figure 2B:
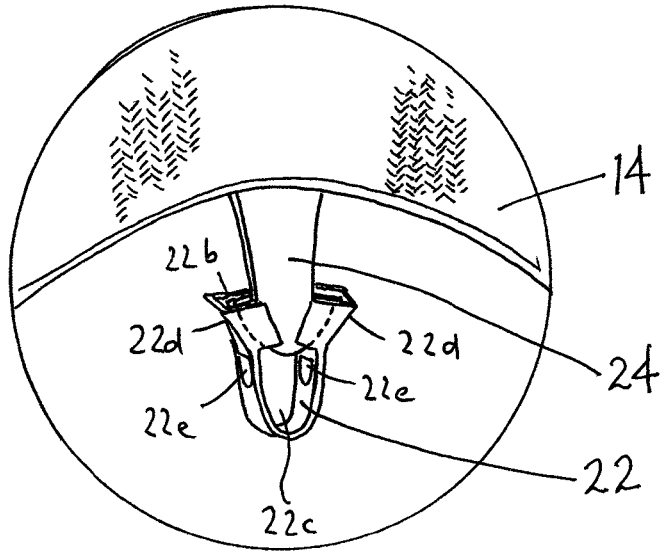
Figure 2C:
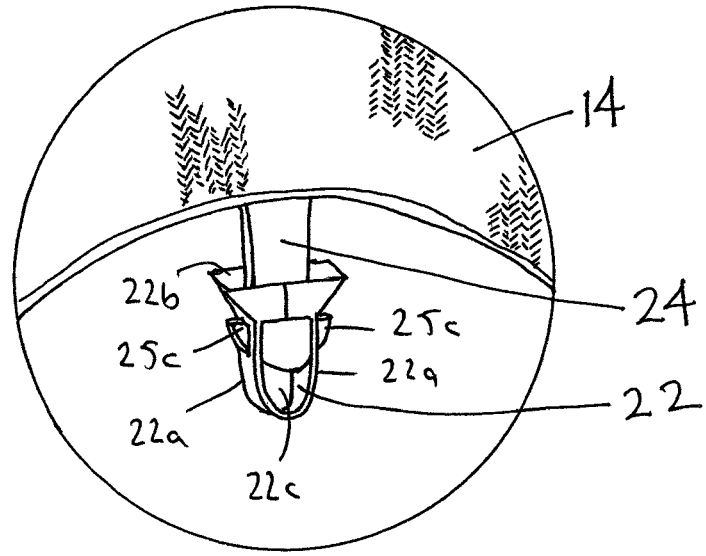

Referring back to FIG. 1, the gasket member 12 includes a plurality of fasteners or receivers 22 for receiving or otherwise engaging engagement members 24 on the valve member 14, e.g., as shown in FIGS. 2A-2C and described further below. The fasteners 22 may be formed as spring-biased clips, for example, as shown in FIGS. 1, 2, 3, 8, 10, 11, 15, and 16. As shown, the gasket member 12 includes three such fasteners 22, e.g., which may be attached at locations corresponding to the commissures of the valve member 14 (and, consequently, the commissures of the tissue annulus within which the gasket member 12 is implanted, as described further below). Alternatively, if desired, the gasket member 12 may include more or fewer fasteners 22 than shown.

Figure 11:
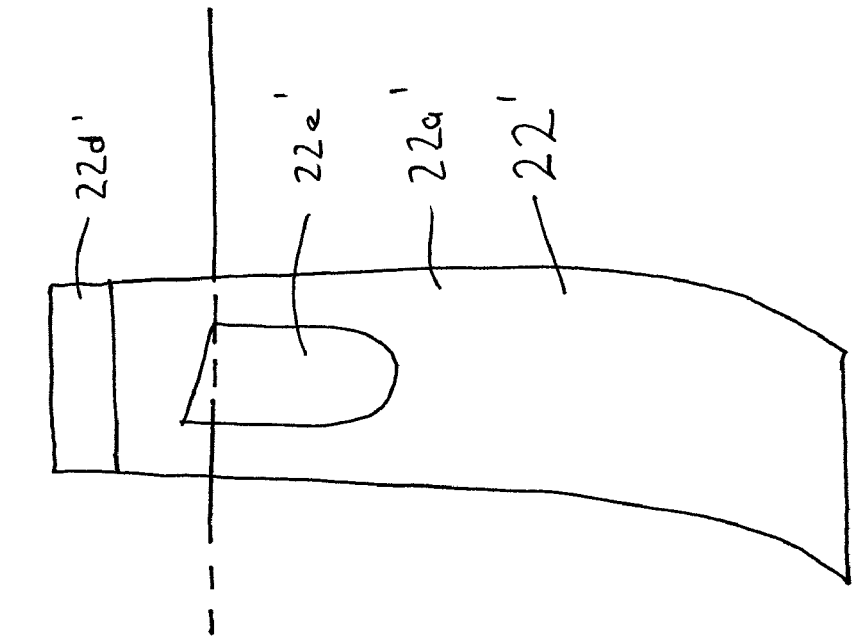
FIGS. 10 and 11 are front and side views, respectively, of a U-shaped spring-biased clip fastener.
Figure 10:
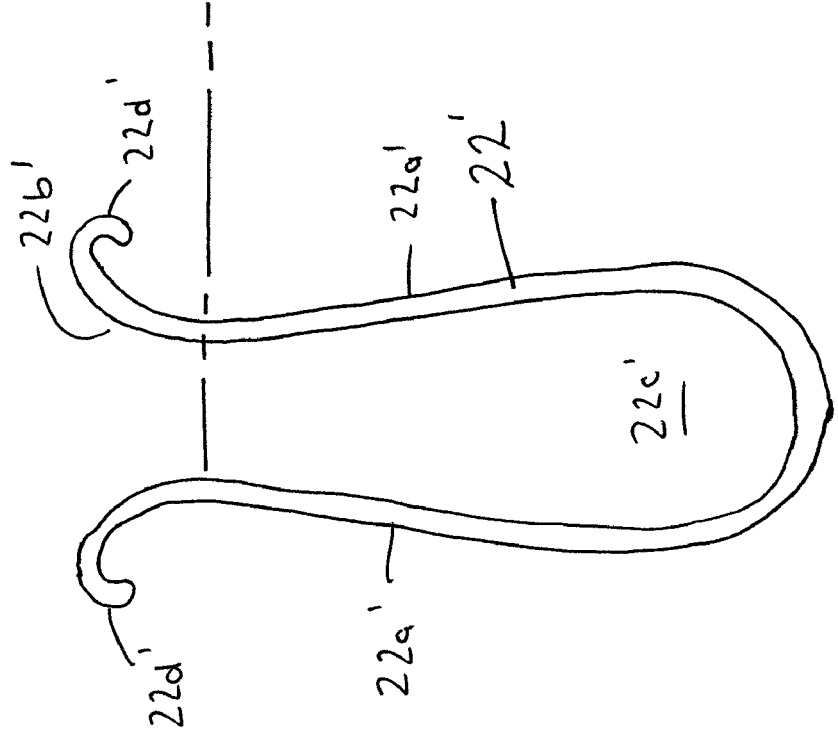

Turning to FIGS. 2-2C, a first embodiment of a fastener 22 is shown, namely a "U" shaped clip that includes a pair of spaced-apart legs 22a defining a funnel-shaped opening 22b and a pocket 22c therebetween. Ends 22d of the opposing legs 22a may be bent away from one another and/or may include front and/or rear surfaces defining the opening 22b, e.g., such that the opening 22b has a larger cross-section than the pocket 22c. Alternatively, the legs 22a may have other shapes and/or configurations. For example, as shown in FIGS. 10 and 11, the legs 22a' may extend generally parallel to one another. Ends 22d' of the legs 22a' may curve outwardly, e.g., to provide rounded surfaces adjacent the opening 22b.' Thus, the ends 22d, 22d' may provide tapered and/or rounded surfaces, which may guide or otherwise facilitate receiving the engagement members 24 (not shown), as explained further below.

In addition, the embodiments shown in FIGS. 2-2C and 10-11, the fasteners 22, 22' include holes or slots 22e, 22e,' e.g., in each leg 22a, 22a' and/or otherwise adjacent the pocket 22c, 22c.' The holes 22e may have upper edges that extend substantially perpendicular to the legs 22a, as shown in FIG. 2, or, alternatively, the holes 22e' may have upper edges that are angled, as shown in FIG. 11. Angled upper edges of the holes 22e' may further guide engagement members 24 (not shown; see, e.g., FIG. 15) into the pocket 22c' and/or bias the engagement members 24 towards one side of the fasteners 22.'

Figure 12:
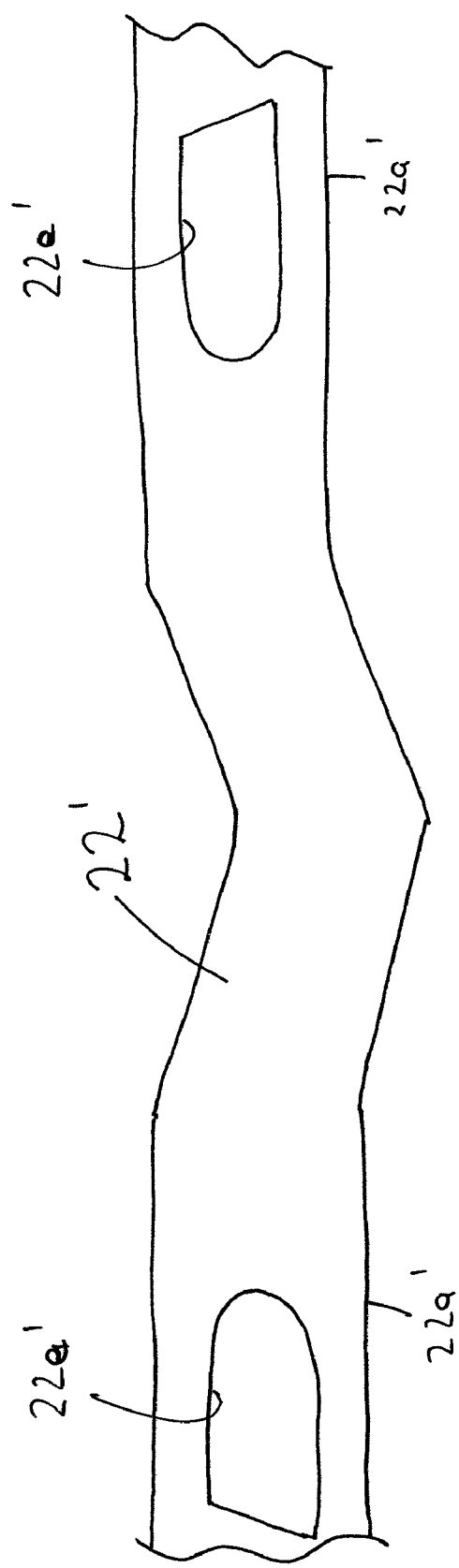
FIG. 12 is a plan view of the fastener of FIGS. 10 and 11, before being formed into a U-shaped clip.
Figure 13:
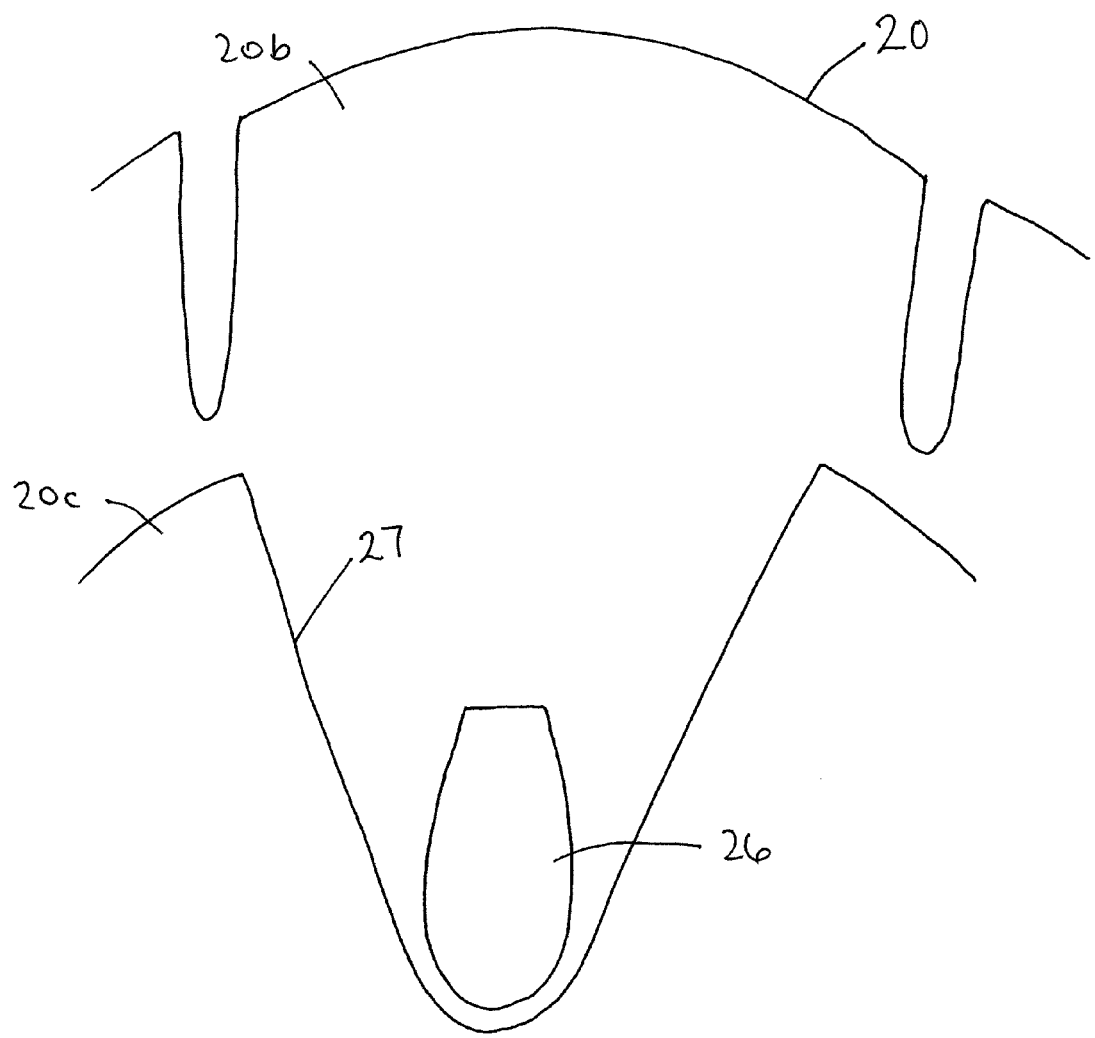
FIGS. 13 and 14 are front and perspective details of a flexible tab or post on the core of FIGS. 7 and 8 for securing a clip fastener to the core.
Figure 14:
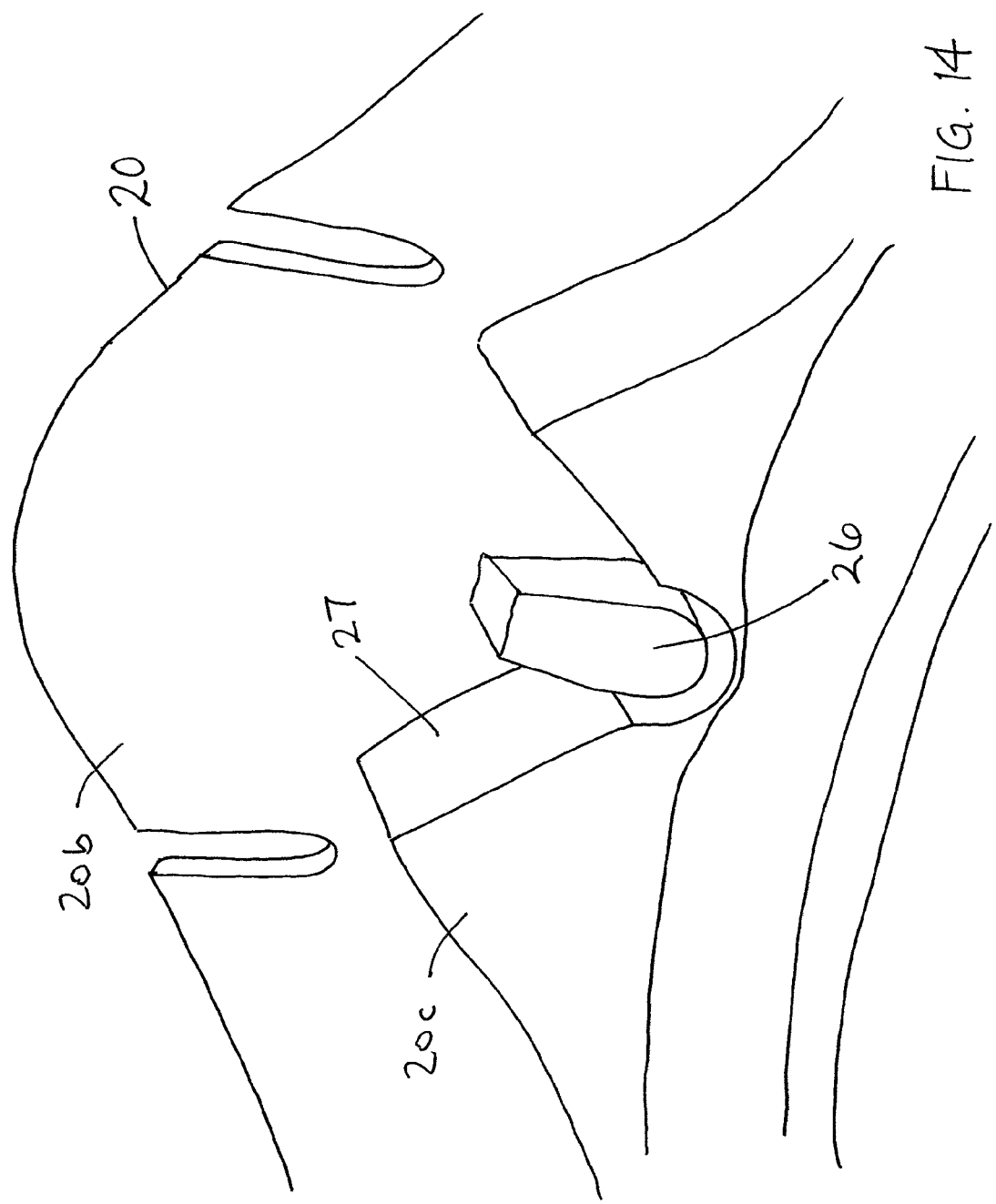

Turning to FIG. 12, each fastener 22' may be formed from a flat sheet of material, e.g., Nitinol or other elastic or superelastic material. For example, the legs 22a' and/or holes 22e' may be stamped, die-cut, laser cut, machined, or otherwise formed from the flat sheet. The legs 22a' may then be bent, roll formed, or otherwise formed into the desired shape, such as that shown in FIGS. 10 and 11.

The fasteners 22 may be embedded, molded, press-fit, or otherwise secured to the gasket member 12. In one embodiment, shown in FIGS. 7, 8, 13, and 14, the gasket member 12 may include a plurality of alignment members or supports 26 onto which the fasteners 22' may be mounted. As shown in FIG. 8, the supports 26 may support the fasteners 22' in a substantially vertical orientation.

The supports 26 may include a post, groove, or the like, e.g., attached to or formed from the core 20a of the cuff 20. For example, as shown in FIGS. 7 and 8, the core 20a may include an upper, relatively thin region 20b and a lower, relatively thick region 20c. These regions 20b, 20c may be provided to provide different flexibility regions in the cuff 20 and/or to enhance sealing between the valve member 14 and gasket member 12, e.g., as described in application Ser. No. 11/069,081, incorporated by reference herein. The supports 26 may be integrally formed when the core 20a is molded, cast, or otherwise formed. Alternatively, the supports 26 may be cut or otherwise formed by removing portions of the lower region 20c, e.g., after molding or otherwise forming the core 20a. In a further alternative, the supports 26 may be attached to the core 20a, e.g., by bonding, sonic welding, using fasteners embedded or inserted through the core 20a, and the like.

Optionally, as shown in FIGS. 7, 8, 13, and 14, tapered channels 27 may be provided above and/or adjacent the supports 26, e.g., formed in the material of the core 20a. For example, the channels 27 may be created when the core 20a is molded or may be created by removing material from the core 20a, e.g., when the supports 26 are formed. The channels 27 may also guide an engagement member 24 (not shown) toward the fastener 22 mounted to the alignment member 26, as explained further below.

Figure 5:
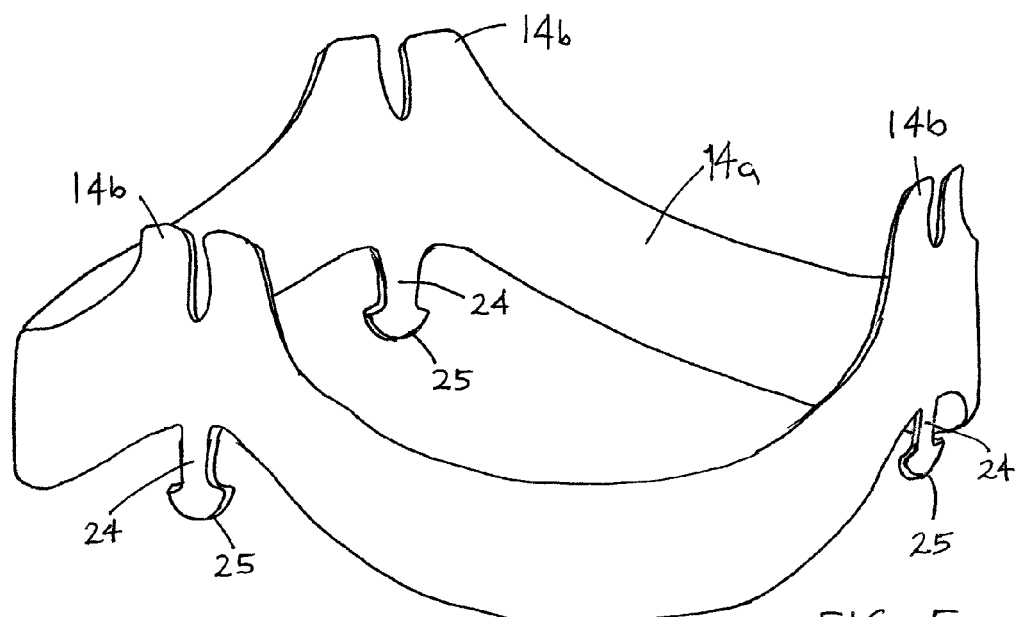
FIGS. 5 and 6 are perspective views of a frame for a valve member, shown before and after being covered with cloth, respectively.
Figure 6:
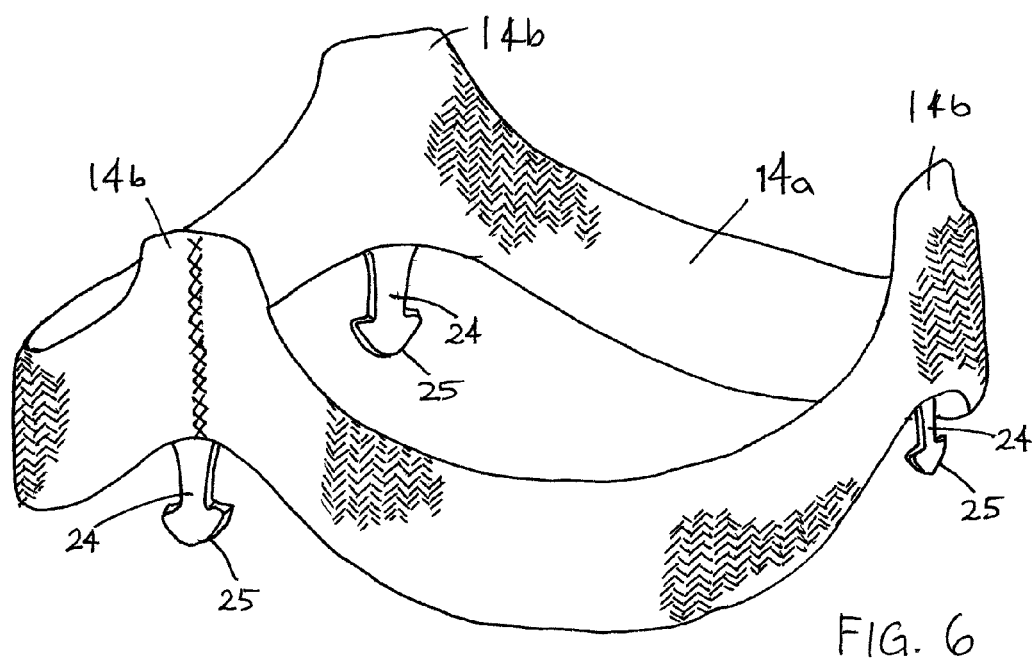

Turning to FIGS. 2, 5, and 6 an exemplary embodiment of the valve member 14 is shown that generally includes a frame 14a carrying a plurality of leaflets 33 or other valve elements (shown in FIG. 2). Turning to FIG. 5, the frame 14a may be formed from substantially rigid or semi-rigid materials, e.g., Nitinol, Elgiloy, stainless steel, plastic, composites, and the like. For example, the frame 14a may be formed from a sheet of Nitinol that is laser cut, stamped, die-cut, or otherwise formed to define the features of the frame 14a frame, e.g., the engagement members 24, commissures 14b, and/or one or more holes or other openings. The frame 14a may be rolled or otherwise formed into an annular shape, e.g., with the ends of the frame 14a attached to one another, e.g., by welding, bonding, fasteners, cooperating connectors, and the like. As shown in FIG. 6, the frame 14a may be substantially covered with cloth, e.g., leaving the engagement members 24 exposed (i.e., without a cloth covering).

As shown in FIG. 2, a plurality of leaflets 33 may be carried by the frame 14a. For example, the leaflets 33 may be tissue leaflets supported by laminate structures (not shown) attached to the frame 14a, such as those disclosed in U.S. Pat. No. 6,371,983 and co-pending application Ser. No. 11/144,254, filed Jun. 3, 2005, the entire disclosures of which are expressly incorporated by reference herein. Alternatively, other valve prostheses may be provided with the engagement member 24, such as mechanical valves, instead of those disclosed Turning to FIG. 9, an exemplary embodiment of an engagement member 24 is shown that may be provided on the frame 14a and/or valve member 14. Generally, the engagement member 24 includes a first end attached or extending from the frame 14a and a second end formed in the shape of a protruding latch or barbed protrusion 25. As shown in FIGS. 5 and 6, the engagement members 24 generally projects downward direction, e.g., substantially vertically from a horizontal plane of the valve member 14. Further, as shown in FIGS. 2 and 3, the engagement members 24 are oriented on the valve member 14 to correspond with their respective mating fasteners 22 in the gasket member 12.

Figure 9:
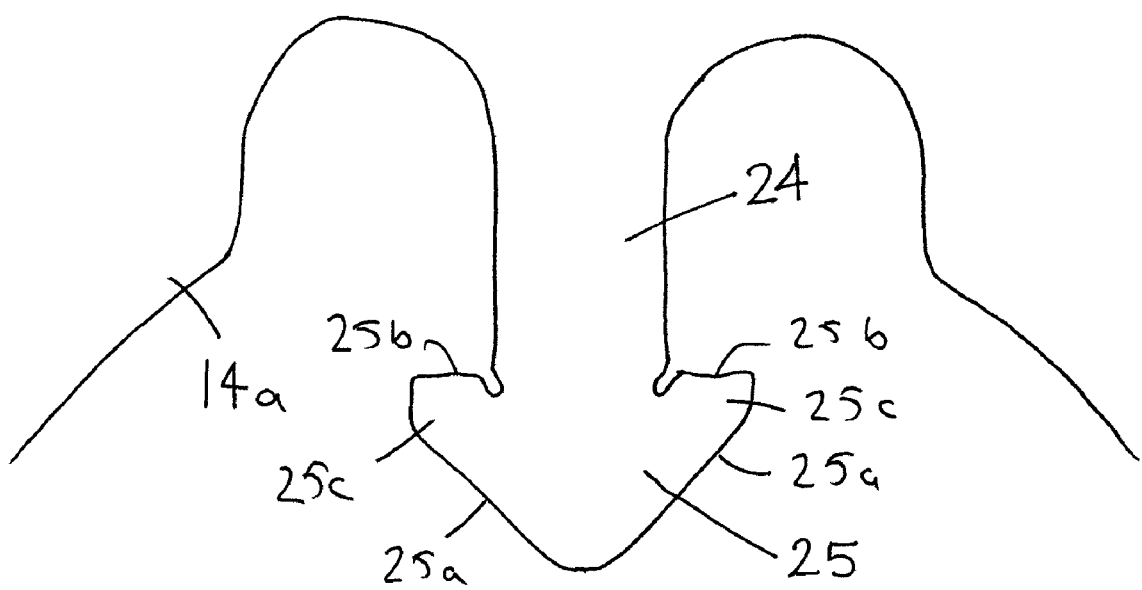
FIG. 9 is a detail of a fastener that may be provided on a frame of a valve member.

Returning to FIG. 9, each engagement member 24 may be formed with a distal head or tip 25 defining one or more tapered first or distal edges 25a and blunt second or proximal edges 25b defining respective tabs or detents 25c. The heads 25 may be formed in the shape of arrows, as shown in FIG. 9, or, alternatively as rounded heads 25, as shown in FIG. 5. As shown in FIGS. 2A-2C and described further below, the heads 25 may be designed to guide or otherwise facilitate inserting the engagement members 24 into the respective fasteners 22, e.g., such that the heads 25 enter the pockets 22c and/or the detents 25c are received in or otherwise engage the hole(s) 22e in the legs 22a of the fasteners 22. In this regard, when the engagement members 24 are inserted into the fasteners 22, the distal heads or tips 25 are locked in position with respect to the fasteners 22, thereby substantially securing the valve member 14 to the gasket member 12.

For example, FIGS. 2A-2C are a series of drawings depicting a single engagement member 24 being inserted into a corresponding fastener 22. As shown in FIG. 2A and explained above, the fastener 22 is a clip that includes a pair of spaced-apart legs 22a defining a funnel-shaped opening 22b and a pocket 22c. As shown in FIG. 2A, the engagement member 24 may be directed towards the fastener 22, e.g., as the valve member 14 is being directed towards the gasket member 12 (not shown; see, e.g., FIG. 3).

The funnel-shaped ends 22d of the legs 22a may facilitate guiding the head 25 of the engagement member 24 into the fastener 22, e.g., by providing a tapering surface for directing the engagement member 24 into fastener 22 even if slightly misaligned. In addition or alternatively, the tapered or rounded distal edges 25a of the head 25 may also guide the head 25 into the opening 22b. As shown in FIG. 2B, the legs 22a of the fastener 22 may spread apart slightly as the engagement member 24 is inserted into the opening 22b. Once the head 25 of the engagement member 24 is pushed further into the fastener 22, i.e., into the pocket 22c, the detents 25c may be aligned with the holes 22e in the legs 22a. Because of the inward bias of the legs 22a of the fastener, the legs 22a may resiliently collapse back, thereby locking the engagement member 24 within the fastener 22.

Figure 15:
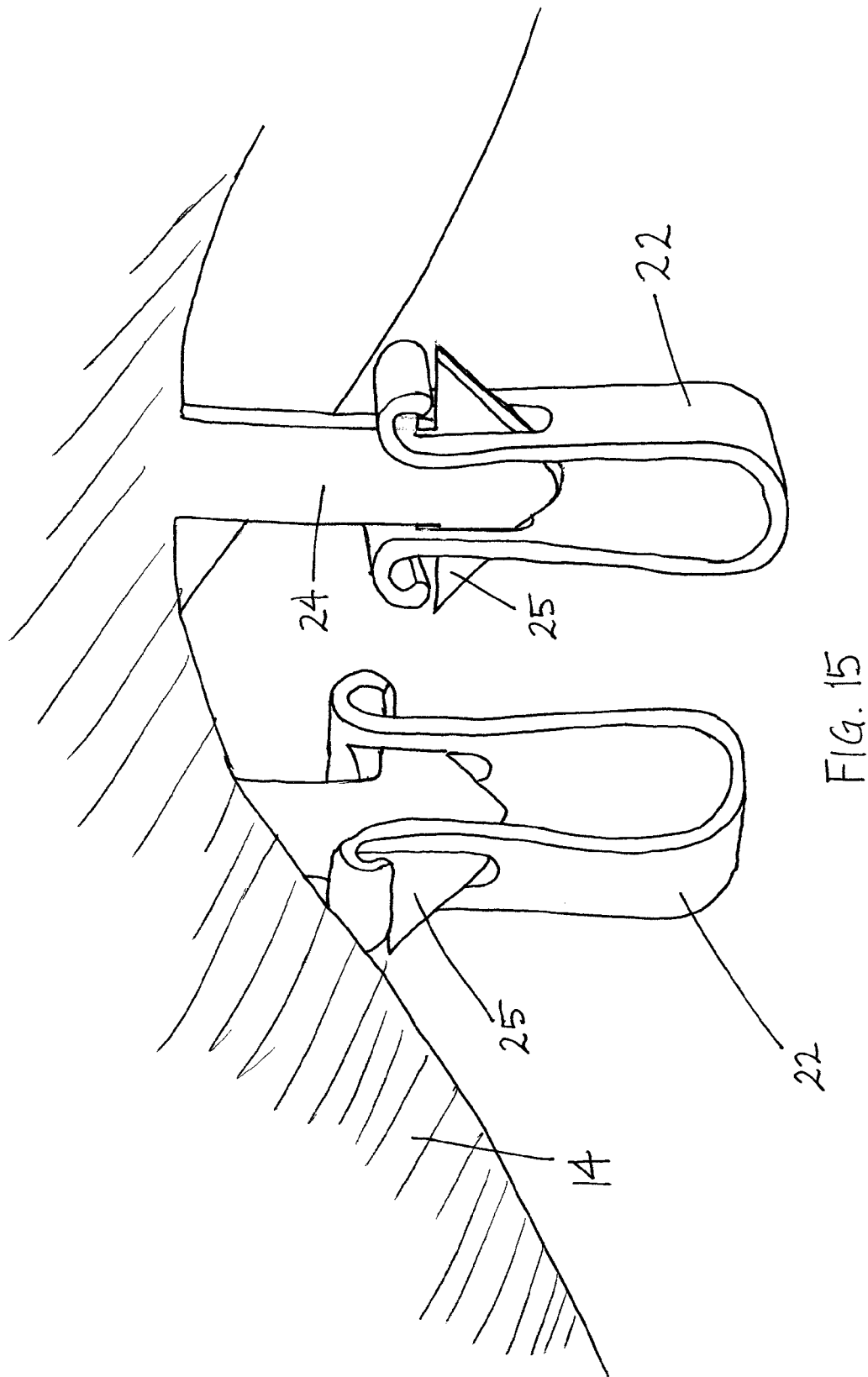
FIG. 15 is a perspective detail of a valve member including fasteners engaged with corresponding fasteners for a gasket member.

In one embodiment, a "snap-fit" is created between the valve member 14 and gasket member 12. The blunt proximal edges 25b of the engagement members 24 prevent removal of the head 25 from the pocket 22c, thereby preventing removal or disengagement of the engagement members 24 from the fasteners 22. In addition, feedback in the form of an audible "click" or tactile "click" may be experienced when the valve member 14 is snapped into the gasket member 12, e.g., as each of the engagement members 24 is engaged with the respective fasteners 22, which may facilitate confirmation that the engagement members 24 are secured within the fasteners 22. FIGS. 3 and 15 also show the valve member 14 secured to the gasket member 12 when the engagement members 24 are engaged with the gasket member 12.

FIG. 3 illustrates an assembled heart valve assembly 10 once the valve member 14 is secured to the gasket member 12, e.g., using three fasteners 22 and corresponding engagement members 24. FIG. 3 also illustrates a clip or fastener passing through the sewing cuff 20, which may be penetrated into surrounding tissue to secure the gasket member 12, as disclosed in co-pending applications Ser. Nos. 10/681,700, filed Oct. 8, 2003 and Ser. No. 11/004,445, filed December, 2004. The entire disclosures of these application are expressly incorporated by reference herein.

During use, the heart valve assembly 10 shown in FIGS. 1-3 may be implanted within a patient's body, e.g., within or adjacent to a biological annulus (not shown). The biological annulus may be the site for replacing an existing natural or previously implanted heart valve, such as a tricuspid, mitral, aortic, or pulmonary valve within a patient's heart (not shown).

Before implanting the heart valve assembly 10, the patient may be prepared for the procedure using known methods. For example, the patient may be placed on cardiopulmonary bypass (CPB), and the patient's heart may be exposed, e.g., by sternotomy, thoracotomy, or other open or minimally invasive procedure. An incision may be created in the blood vessel above the valve being replaced (not shown), e.g., the aorta for an aortic valve replacement, in order to access the annulus 90. The existing natural or prosthetic heart valve and/or leaflets (also not shown) may then be removed from the annulus 90 using known methods.

A heart valve assembly 10, including a gasket member 12 and a valve member 14 may be selected based upon the anatomy encountered, e.g., having a plurality of lobes, matching the lobes of the biological annulus and/or having a cross-sectional dimension corresponding to the interior cross-section of the biological annulus. Optionally, a gasket member 12 and/or valve member 14 may selected having a size that is larger than the biological annulus. For example, the gasket member 12 may have a diameter in its relaxed condition that is slightly larger than the biological annulus, e.g., such that the gasket member 12 may at least partially dilate the biological annulus upon implantation. In addition or alternatively, the valve member 14 may have a diameter or other cross-section that is substantially larger than the biological annulus, e.g., for supra-annular or intra-sinus implantation, which may accommodate the larger size.

The gasket member 12 may be introduced into the patient's body and advanced into the biological annulus, e.g., using a delivery tool (not shown). The gasket member 12 may be advanced until the annular ring 18 extends at least partially into the biological annulus. In one embodiment, the annular ring 18 may extend through the biological annulus, i.e., with a lower edge of the annular ring 18 disposed within the sub-annular space below the biological annulus. Optionally, the gasket member 12 may include a flexible skirt (not shown) that may surround and/or extend from the annular ring 18 through the biological annulus. The skirt may be biased to extend outwardly to provide a smooth transition and/or enhance a seal between the gasket member 12 and the biological annulus.

Optionally, the gasket member 12 may then be expanded or at least partially released within the biological annulus, e.g., to dilate tissue surrounding the biological annulus or otherwise direct the surrounding tissue outwardly. With the annular ring 18 deployed within the biological annulus, the sewing cuff 20 may contact the tissue surrounding the supra-annular space above the biological annulus. One or more fasteners (such as fastener 96 shown in FIG. 3), e.g., clips or sutures, may be directed through the gasket member 12 into the tissue above and/or surrounding the biological annulus.

With the gasket member 12 secured within the biological annulus, the valve member 14 may then be advanced into the patient's body towards the biological annulus. The valve member 14 may be oriented to align the commissures 14b with the commissures within the biological annulus, and/or to align the engagement members 24 with the fasteners 22. Optionally, the valve member 14 and/or gasket member 12 may include markers and the like (not shown) to facilitate properly orienting the valve member 14. Exemplary markers and methods for using them are disclosed in co-pending application Ser. No. 10/765,725, filed Jan. 26, 2004, the entire disclosure of which is expressly incorporated by reference herein. Alternatively, the gasket member 12 may include guide rails or members (not shown) over which the valve member 14 may be advanced, such as those disclosed in application Ser. No. 10/765,725 or application Ser. No. 60/748,639, filed Dec. 7, 2005, the entire disclosure of which is also expressly incorporated by reference herein. In this alternative, the engagement members 24 may include holes, passages, or other features (not shown) for slidably receiving the guide members therethrough.

As described above, the engagement members 24 may then be engaged with the respective fasteners 22. For example, the valve member 14 may be tilted slightly to engage a first of the engagement members 24 with the respective fastener 22. The valve member 14 may then be tilted to successively engage each of the other sets of engagements members 24 and fasteners 22. Alternatively, the valve member 14 may be advanced such that the engagement members 24 and fasteners 22 engage substantially simultaneously. If guide members are used, the guide members may be cut, broken, or otherwise severed to allow their removal. Any tools may be removed, leaving the assembled heart valve assembly 10 within the biological annulus.

It will be appreciated that elements or components shown with any embodiment herein are exemplary for the specific embodiment and may be used on or in combination with other embodiments disclosed herein. It will also be appreciated that components, e.g., the fasteners 22 and/or engagement members 24, may be interchanged, provided on either of the gasket member 12 and valve member 14, yet still allow the valve member 12 to be secured to the gasket member 14.

While embodiments of the present invention have been shown and described, various modifications may be made without departing from the scope of the present invention. The invention, therefore, should not be limited, except to the following claims, and their equivalents.

We claim:

1. A prosthesis for receiving a valve prosthesis, comprising:
   an annular ring advanceable into a tissue annulus;
   a sewing cuff extending radially from the annular ring;
   a plurality of receivers secured to the sewing cuff, each receiver comprising a pair of legs defining a pocket, the legs being deflectable away from one another to accommodate receiving an engagement member from a valve prosthesis in the pocket, the legs being resiliently deflectable towards one another after an engagement member is received in the pocket for securing the engagement member to the receiver; and wherein the legs of each receiver comprise tapered upper edges for guiding an engagement member into the pocket.

2. The prosthesis of claim 1, wherein the sewing cuff comprises a core to which the receivers are secured, the sewing cuff further comprising a layer of fabric overlying the core.

3. The prosthesis of claim 2, wherein the layer of fabric comprises an opening overlying each receiver for receiving an engagement member therethrough.

4. A prosthesis for receiving a valve prosthesis, comprising:

an annular ring advanceable into a tissue annulus;

a sewing cuff extending radially from the annular ring;

a plurality of receivers secured to the sewing cuff, each receiver comprising a pair of legs defining a pocket, the legs being deflectable away from one another to accommodate receiving an engagement member from a valve prosthesis in the pocket, the legs being resiliently deflectable towards one another after an engagement member is received in the pocket for securing the engagement member to the receiver, wherein the receivers comprises spring-biased clips mounted to posts on the sewing cuff.

5. A prosthetic heart valve, comprising:

a gasket member comprising an annular ring advanceable into a tissue annulus, and a sewing cuff extending radially from the annular ring;

a valve member comprising a frame carrying a plurality of valve elements;

a plurality of engagement members extending from one of the gasket member and the valve member; and a plurality of receivers on the other of the gasket member and the valve member, each receiver comprising a pair of legs defining a pocket, the legs being deflectable away from one another to accommodate receiving a respective engagement member in the pocket, the legs being resiliently deflectable towards one another after the engagement member is received in the pocket for securing the engagement member to the receiver, thereby securing the valve member relative to the gasket member, wherein the sewing cuff comprises a flexible core, and wherein the receivers are attached to the core, and wherein the receivers comprises spring clips attached to mounts extending from the core.

6. The prosthetic heart valve of claim 5, wherein the engagement members extend from the frame of the valve member, and the receivers are attached to the gasket member.

7. The prosthetic heart valve of claim 6, wherein the engagement members are integrally formed with the frame.

8. The prosthetic heart valve of claim 5, wherein each engagement member comprises at least one detent, and each receiver comprises at least one hole for receiving the respective detent therein when the engagement member is received in the pocket.

9. The prosthetic heart valve of claim 5, wherein each engagement member comprises a tapered or rounded first edge to guide the engagement member into the respective pocket, and a substantially blunt second edge to prevent the engagement member from being removed subsequently from the respective pocket.

10. The prosthetic heart valve of claim 9, wherein each engagement member comprises a pair of detents including tapered or rounded first edges and substantially blunt second edges.

11. The prosthetic heart valve of claim 10, wherein the detents are disposed opposite one another on the engagement member.

12. A prosthetic heart valve, comprising:

a gasket member comprising an annular ring advanceable into a tissue annulus, and a sewing cuff extending radially from the annular ring;

a valve member comprising a frame carrying a plurality of valve elements;

a plurality of engagement members extending from one of the gasket member and the valve member, the engagement members comprising tabs including tapered first edges and substantially blunt second edges; and a plurality of receptacles on the other of the gasket member and the valve member comprising a pocket for receiving respective engagement members therein, each receptacle comprising one or more tapered surfaces for guiding a respective engagement member into the receptacle, the substantially blunt second edges preventing removal of the engagement members from the receptacles, wherein the sewing cuff comprises a flexible core, and wherein the receptacles comprises spring clips attached to mounts extending from the core.

13. The prosthetic heart valve of claim 12, wherein the plurality of receptacles are attached to the flexible core of the gasket member around a periphery thereof.

14. The prosthetic heart valve of claim 13, wherein the receptacles are attached at locations corresponding to commissures of the valve member.

15. The prosthetic heart valve of claim 12, wherein the engagement members extend from the frame of the valve member.

16. The prosthetic heart valve of claim 15, wherein the engagement members are integrally formed with the frame.

17. The prosthetic heart valve of claim 12, wherein each receptacle comprises at least one hole for receiving a respective tab therein when the engagement member is received in the receptacle.

18. The prosthetic heart valve of claim 12, wherein each engagement member comprises a pair of tabs including tapered first edges and substantially blunt second edges, the tabs disposed opposite one another on the engagement member.

19. The prosthetic heart valve of claim 12, wherein each receptacle comprises a leg that is resiliently deflectable to accommodate receiving a respective engagement member in the pocket of the receptacle.

20. The prosthetic heart valve of claim 19, wherein the leg is deflectable from an original position to accommodate receiving the respective engagement member in the pocket, and the leg is resiliently biased to return to the original position to secure the engagement member within the receptacle.

21. The prosthetic heart valve of claim 12, wherein each receptacle comprises funnel-shaped ends defining the tapered surfaces.

22. The prosthetic heart valve of claim 12, wherein the receptacles are configured to provide an audible click or tactile click when the engagement members are engaged with the respective fasteners.

23. The prosthetic heart valve of claim 12, wherein each receptacle comprises at least one feature for engaging with the substantially blunt edge of a respective tab to prevent removal of the engagement member from the receptacle.

24. The prosthetic heart valve of claim 12, wherein the engagement members are integrally formed with one of the valve member and the gasket member, and the receptacles are attached to the other of the valve member and the gasket member.

* * * * *